United States Patent
Sorensen et al.

(10) Patent No.: US 8,029,536 B2
(45) Date of Patent: Oct. 4, 2011

(54) MULTIPLE OFFSET EYELET SUTURE ANCHOR

(75) Inventors: Peter K. Sorensen, Salem, MA (US); Paul V. Fenton, Jr., Marblehead, MA (US)

(73) Assignee: Tornier, Inc., Edina, MN (US)

( * ) Notice: Subject to any disclaimer, the term of this patent is extended or adjusted under 35 U.S.C. 154(b) by 490 days.

(21) Appl. No.: 11/273,078

(22) Filed: Nov. 14, 2005

(65) Prior Publication Data
US 2007/0112352 A1    May 17, 2007

(51) Int. Cl.
A61B 14/04 (2006.01)
(52) U.S. Cl. .............. 606/232; 606/74; 606/218
(58) Field of Classification Search .......... 606/232, 606/218, 308, 311–312, 331, 74, 908, 916
See application file for complete search history.

(56) References Cited

U.S. PATENT DOCUMENTS

| | | | |
|---|---|---|---|
| 5,370,662 A * | 12/1994 | Stone et al. | 606/232 |
| 5,417,712 A * | 5/1995 | Whittaker et al. | 606/232 |
| 5,443,482 A * | 8/1995 | Stone et al. | 606/232 |
| 5,584,835 A * | 12/1996 | Greenfield | 606/232 |
| 5,690,676 A * | 11/1997 | DiPoto et al. | 606/232 |
| 5,720,766 A * | 2/1998 | Zang et al. | 606/232 |
| 5,814,070 A * | 9/1998 | Borzone et al. | 606/232 |
| 5,824,011 A * | 10/1998 | Stone et al. | 606/232 |
| 6,045,573 A * | 4/2000 | Wenstrom et al. | 606/232 |
| 6,139,565 A * | 10/2000 | Stone et al. | 606/232 |
| 6,149,653 A * | 11/2000 | Deslauriers | 606/232 |
| 6,168,598 B1 * | 1/2001 | Martello | 606/74 |
| 6,267,766 B1 * | 7/2001 | Burkhart | 606/232 |
| 6,508,830 B2 * | 1/2003 | Steiner | 606/232 |
| 6,517,542 B1 * | 2/2003 | Papay et al. | 606/232 |
| 6,540,750 B2 * | 4/2003 | Burkhart | 606/232 |
| 6,610,080 B2 * | 8/2003 | Morgan | 606/232 |
| 6,648,892 B2 * | 11/2003 | Martello | 606/319 |
| 6,656,183 B2 * | 12/2003 | Colleran et al. | 606/232 |
| 6,685,728 B2 * | 2/2004 | Sinnott et al. | 606/232 |
| 6,743,233 B1 * | 6/2004 | Baldwin et al. | 606/323 |
| 6,773,436 B2 * | 8/2004 | Donnelly et al. | 606/232 |
| 7,163,540 B2 * | 1/2007 | Martello | 606/319 |
| 7,320,701 B2 * | 1/2008 | Haut et al. | 606/232 |
| 7,588,587 B2 * | 9/2009 | Barbieri et al. | 606/232 |
| 7,615,061 B2 * | 11/2009 | White et al. | 606/148 |
| 7,713,285 B1 * | 5/2010 | Stone | 606/232 |
| 2002/0022840 A1 * | 2/2002 | Martello | 606/60 |
| 2002/0120292 A1 * | 8/2002 | Morgan | 606/232 |
| 2004/0082956 A1 * | 4/2004 | Baldwin et al. | 606/73 |
| 2004/0098053 A1 * | 5/2004 | Tran | 606/232 |
| 2004/0133239 A1 * | 7/2004 | Singhatat | 606/232 |
| 2004/0230196 A1 * | 11/2004 | Martello | 606/73 |
| 2004/0254580 A1 * | 12/2004 | Boock et al. | 606/73 |
| 2005/0288682 A1 * | 12/2005 | Howe | 606/104 |
| 2006/0100630 A1 * | 5/2006 | West, Jr. | 606/73 |
| 2006/0122608 A1 * | 6/2006 | Fallin et al. | 606/72 |

* cited by examiner

Primary Examiner — Darwin Erezo
Assistant Examiner — Mark Mashack
(74) Attorney, Agent, or Firm — Faegre & Benson LLP

(57) ABSTRACT

A suture anchor for securing soft tissue to bone may include a threaded body, a head extending along a longitudinal axis, and a plurality of eyelets that extend though the anchor head and that are each configured to receive a suture. The eyelets are offset from one another along an axis that is transverse to the longitudinal axis of the suture anchor. Each eyelet may have a desired shape and cross section. Surgical kits including one or more suture anchors and one or more surgical tools are also described.

43 Claims, 15 Drawing Sheets

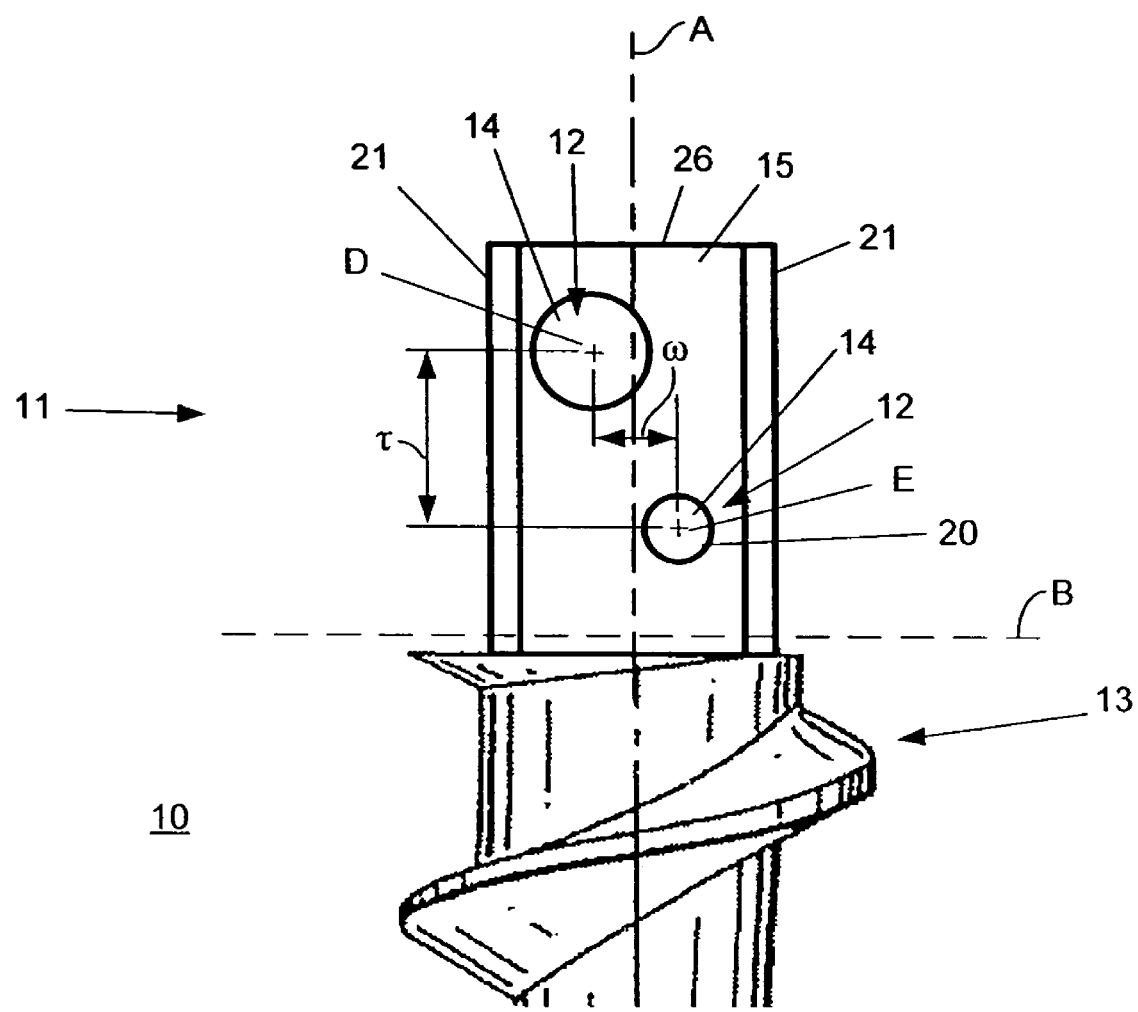

FIG. 14
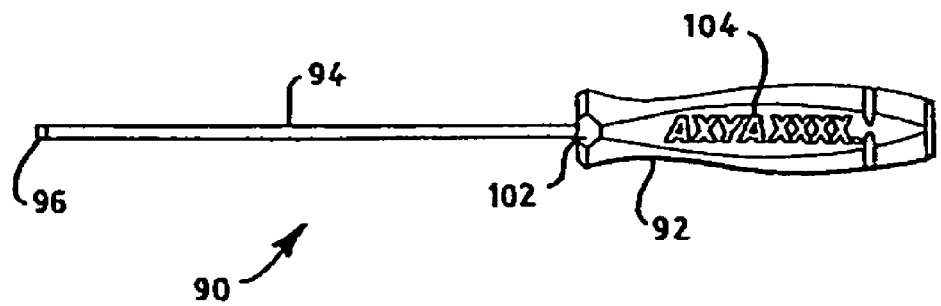
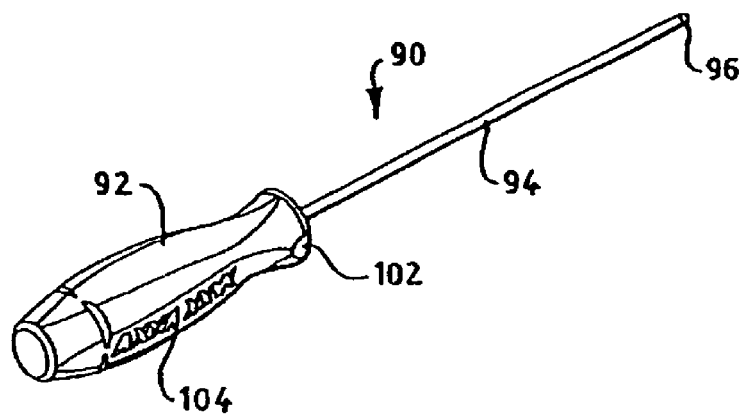
FIG. 15
FIG. 17
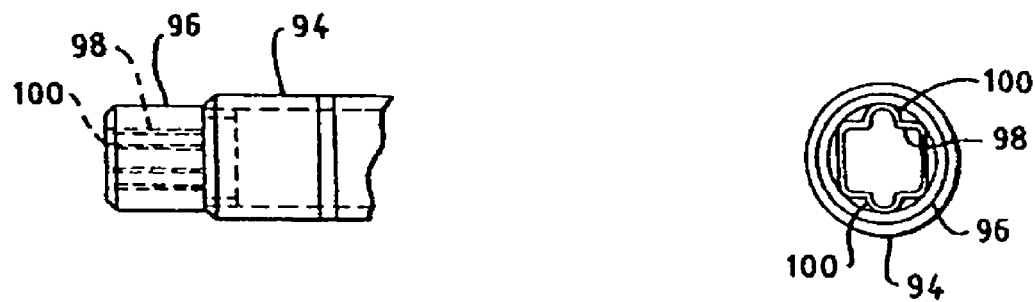
FIG. 16

MULTIPLE OFFSET EYELET SUTURE ANCHOR

BACKGROUND

When biological soft tissue, such as a ligament, tendon, or cartilage, becomes separated from related bone, surgical procedures are commonly employed for reattachment of the soft tissue. Various devices, including sutures, screws, staples, wedges, and plugs have been used to secure soft tissue to bone. Additionally, structures known as suture anchors have been developed for this purpose.

Some suture anchors are designed to be inserted into a pre-drilled hole, while other suture anchors are threaded and self-tapping. Some suture anchors include an eyelet for receiving a suture, while other anchors are cylindrical and adapted for holding a knotted piece of suture, while still other anchors include a strand of suture insert molded in the anchor. Certain suture anchors having one or more generally parabolic eyelets are described in U.S. Pat. No. 6,610,080 to Morgan, the contents of which are incorporated herein by reference. The Morgan patent describes suture anchor arrangements having multiple eyelets for securing two or more sutures to a desired location on a bone, but these arrangements may be susceptible to breakage or structural failure around the eyelets under certain conditions.

What is needed, therefore, is an improved suture anchor capable of securing multiple sutures for reattachment of soft tissue to bone. What are also needed are kits including such suture anchors and arthroscopic apparatus for surgery using such anchors.

SUMMARY

The needs described above are addressed by the present disclosure, which is directed to multiple offset eyelet suture anchors and related surgical kits. The suture anchors include multiple eyelets that are offset in a direction transverse to a longitudinal axis of the anchor for holding multiple sutures, such as in reattachment surgery securing soft tissue to bone.

One arrangement of a suture anchor according the present disclosure may include an anchor head and a threaded body. The head may include two or more eyelets each defining a void region extending between opposite lateral surfaces, each eyelet being adapted to receive a suture. Within the anchor head, each eyelet is offset, or spaced apart, from the other a distance along the longitudinal axis A and also a distance in a direction transverse to the longitudinal axis A. Such arrangements may provide increased strength and resistance to failure, such as shearing of material around the eyelets.

Each eyelet may be shaped as desired. In some arrangements, for example, an eyelet may have a parabolic and/or elliptical cross section and include two outer void regions and a central void region extending between the outer void regions along a suture-direction axis extending transverse to the longitudinal axis of the body. For such parabolic cross section eyelets, an outer void region may extend from one of the lateral surfaces of the anchor head and have a central axis forming an acute angle with the longitudinal axis of the body. For further example, each eyelet may have a surface shaped as a segment of a desired conic surface extending about the central axis of the outer void region and tapering inward towards the longitudinal axis of the body. The void region of each eyelet may extend about a central axis having a desired configuration, e.g., a straight line or a curved line. Curved-line configurations may have any suitable shape, e.g., serpentine, sinusoidal, irregular, etc.

Another arrangement of the present disclosure may include a surgical kit including a suture anchor according to the present disclosure and further including a drill guide. The drill guide may have a handle and a hollow guide shaft rotatably secured to the handle, the guide shaft having a tip and an alignment window adjacent the tip. An adjustment wheel may extend radially from the shaft. Within such kits, the drill guide may include a button that is positioned within the handle and that may be movable to a locked position preventing rotation of the adjustment wheel.

The kit may include at least one length of suture. The suture may be a monofilament or may include multiple filaments. One end of the length of suture may be deformed. The suture may be bio-compatible. The suture of the kit may be bio-absorbable.

In certain arrangements, a kit may include a tubular drive tool having a handle and a tube extending from the handle to a distal end. A drive socket may be attached to the distal end of the tube and may include inwardly facing surfaces for gripping outwardly facing surfaces of an anchor head of a suture anchor for transferring torque from the drive tool to the suture anchor. The inwardly facing surfaces may include recesses positioned for alignment with the outer void regions of an eyelet of the anchor and sized to receive a suture passing through the eyelet.

Additional advantages and aspects of suture anchors and surgical kits according to the present disclosure will be readily apparent to those skilled in the art from the following detailed description, wherein arrangements of the present invention are shown and described.

The present disclosure, in addition, is capable of other and different arrangements, and its several details are susceptible of modification in various obvious respects, all without departing from the spirit of the present disclosure. Accordingly, the drawings and description are to be regarded as illustrative in nature, and not as limitations.

BRIEF DESCRIPTION OF THE DRAWINGS

FIG. 12 is a frontal view of an alternate configuration of a suture anchor head.

FIG. 14 is a side elevation view of a drive tool suitable for use with suture anchors according to the present disclosure;

FIG. 15 is a perspective view of the drive tool of FIG. 14;

FIG. 16 is an enlarged elevation side view of a tip of the drive tool of FIG. 14;

FIG. 17 is an enlarged elevation end view of the tip of the drive tool of FIG. 14.

In the figures, like reference characters designate identical or corresponding components and reference characters, including axes, angles and units.

DETAILED DESCRIPTION

Arrangements of the present disclosure are directed to suture anchors having multiple eyelets that are offset along an axis transverse to a longitudinal axis of the anchor. The offset eyelets may provide additional material to withstand forces in particular directions while still providing a suture anchor that can hold two or more sutures to a desired location, such as a particular location on a patient's bone. The offset configurations of the two or more eyelets allows for increased suture-to-anchor strength, e.g., resistance to the suture shearing through the anchor head. A suture anchor as disclosed herein can be used with suitable types of sutures including monofilament sutures, braided sutures, absorbable sutures, and non-absorbable sutures.

Figure 1:
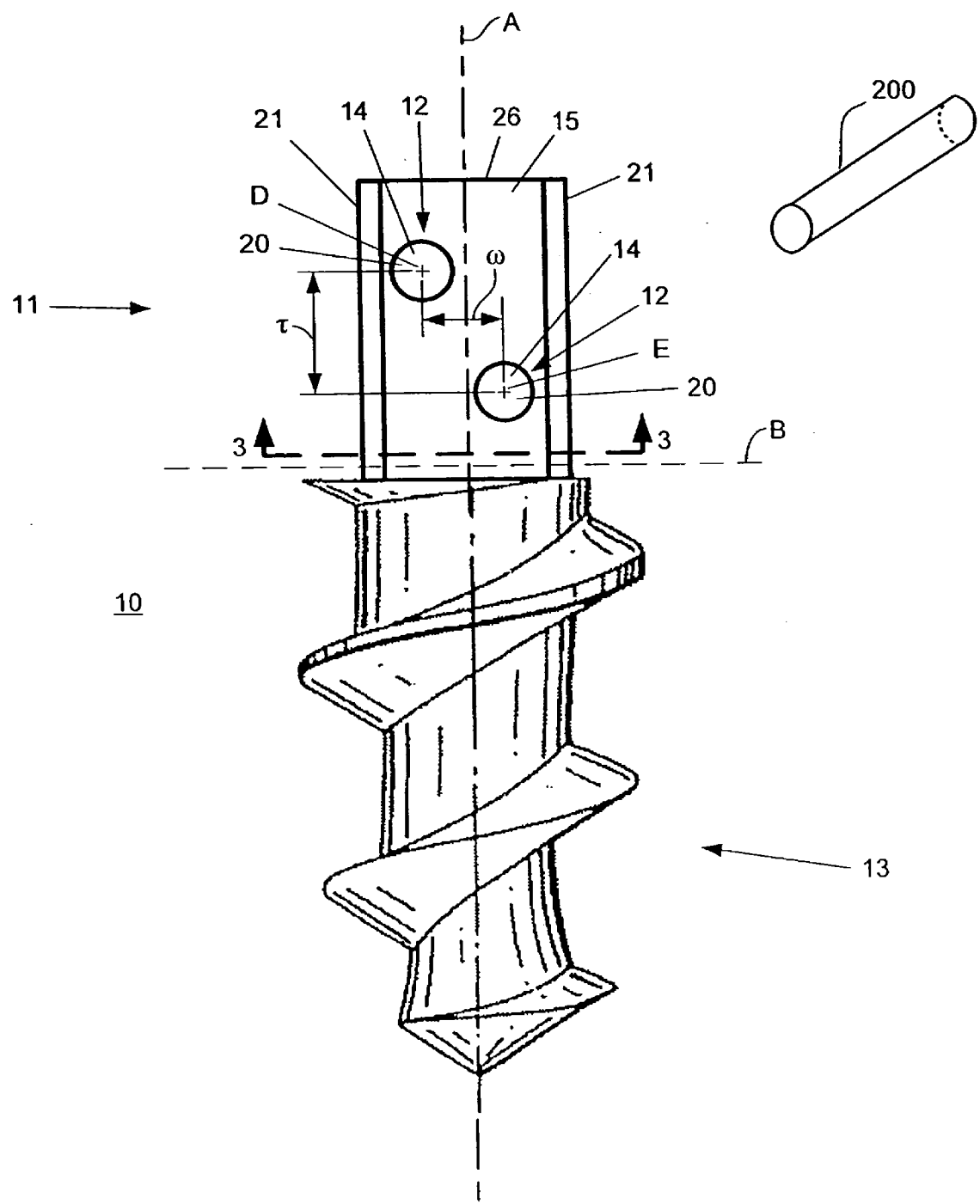
FIG. 1 is a frontal view of a suture anchor constructed in accordance with the present disclosure.

Referring to FIG. 1, a frontal view is shown of a suture anchor 10 constructed in accordance with an arrangement of the present disclosure. The anchor 10 includes an anchor head 11 and a threaded body 13 extending along a longitudinal axis A. The anchor head 11 also includes at least two eyelets 12 that extend between lateral surfaces 15 of the head 11. Each eyelet 12 has two openings 20 and a central void region 14 for securing a length of suture 200 to bone (not shown). In addition to the lateral surfaces, the anchor head 11 may include a number of sides 21 and a top surface 26 to achieve a desired cross-sectional shape of the anchor head, e.g., one suited for a driving tool shown in FIGS. 13-18.

Within the anchor head 11, each eyelet 12 is offset, or spaced apart, from the other a distance τ along the longitudinal axis A and also a distance ω in a direction transverse to the longitudinal axis A, for example, as indicated by locations of respective eyelet central axes D and E. The void region 14 of each eyelet may be aligned substantially parallel with a suture-direction axis (e.g., axis C shown in FIG. 2) of the anchor 10. Lateral axis B, transverse to longitudinal axis A is shown for reference. While the defining surface of the central void region 14 is preferably cylindrical, it can be any other suitable shape, e.g., concave, variable in cross section, etc. Because of the locations of the eyelets 12 relative to one another within the suture anchor 10, the void regions 14 are separate and discrete.

As described, the suture anchors 10 include a threaded body 13 for insertion of the anchor 10 into a bone at a desired location. The threaded body 13 may include a suitable number of threads having a desired pitch. In certain arrangements, the threaded body 13 can be self-tapping and can include a self-drilling tip if desired.

Figure 2:
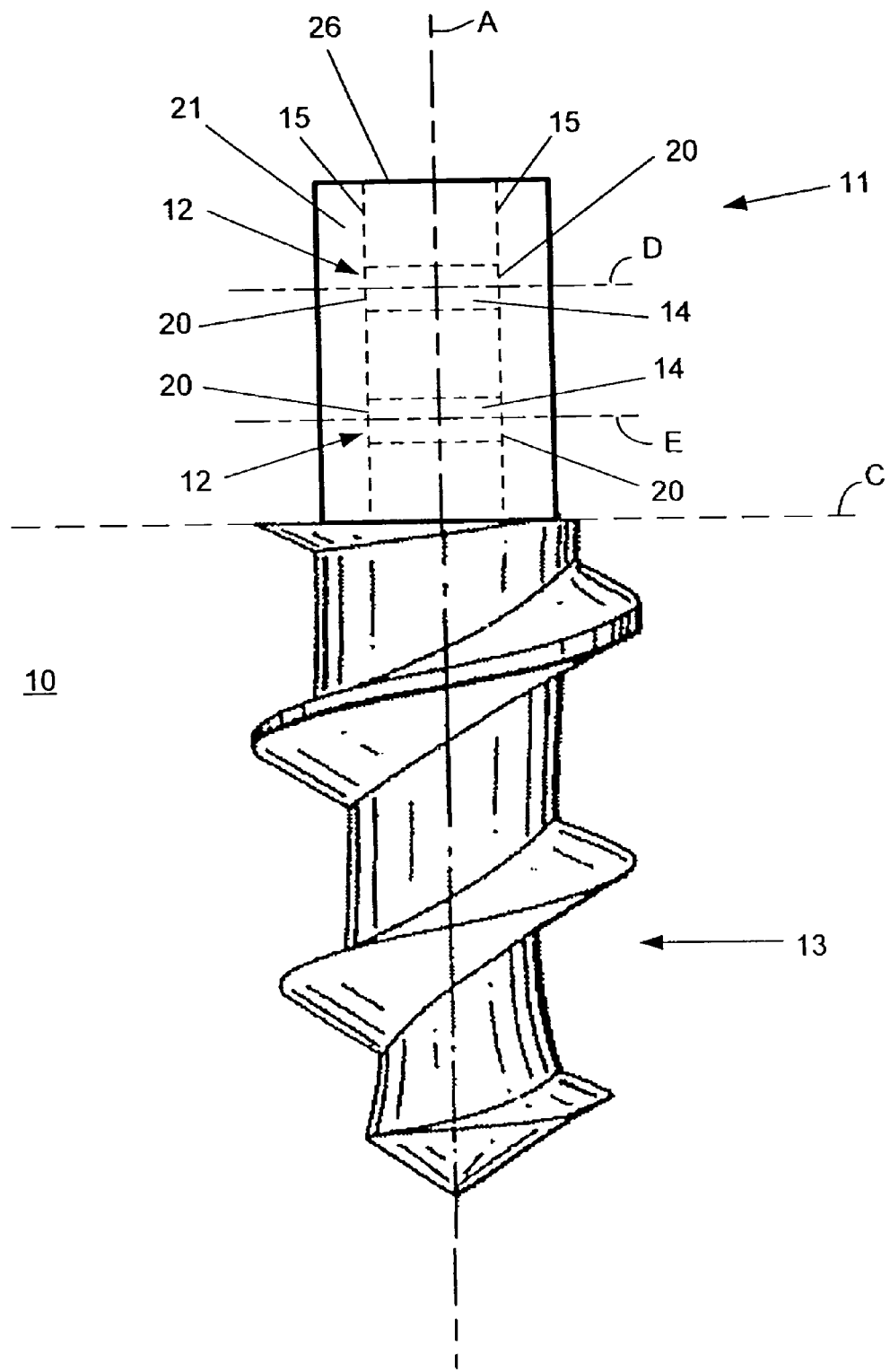
FIG. 2 is a side view of the suture anchor of FIG. 1.

FIG. 2 is a side view of the suture anchor 10 of FIG. 1 showing the relationship of the eyelets 12 within the anchor head and relative to the threaded body 13. The eyelets 12 are shown at unique locations along the longitudinal axis A of the anchor 10, with one eyelet located in closer proximity to the threaded body 13. As shown by respective central axes D and E, the void region 14 of each eyelet 12 extends along suture-direction axis C (which is substantially orthogonal to lateral axis B shown in FIG. 1) and between the lateral surfaces 15 of the anchor head 11.

Figure 3:
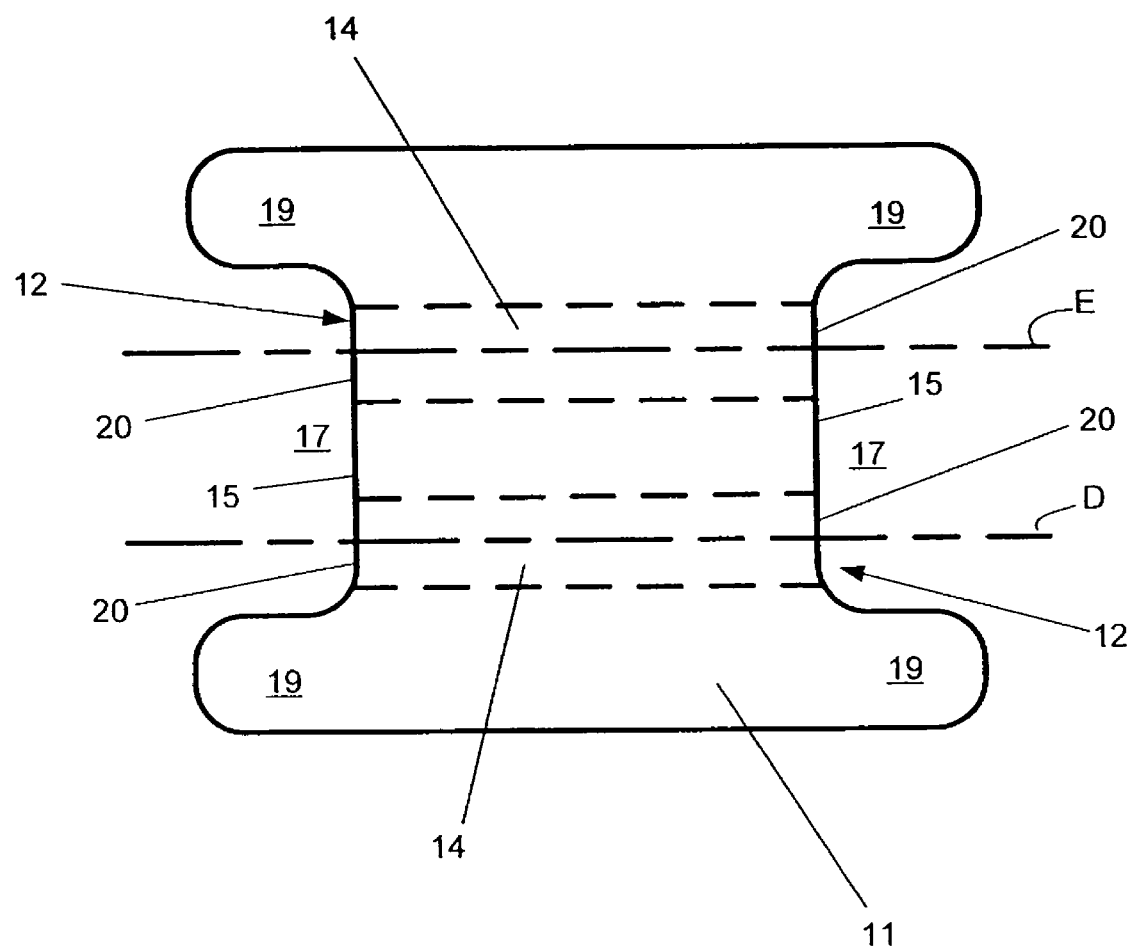
FIG. 3 is a sectional view of the anchor head of the suture anchor of FIG. 1 in the direction of cutting plane 3-3.

FIG. 3 is a sectional view of the anchor head 11 of FIG. 1 in the direction of cutting plane 3-3. The void regions 14 are aligned along respective central axes D and E, extending between lateral surfaces 15 of the anchor head 11. The lateral surfaces 15 may be configured to form recesses 17, which may facilitate protection of sutures and/or application of the anchor 10 by a surgical tool, e.g., arthroscopic tools 70 and 90 shown in FIGS. 13-18. Recesses 17 may be formed on opposing sides of the anchor head 11 between pairs of ribs 19 extending along the C axis.

Figure 4:
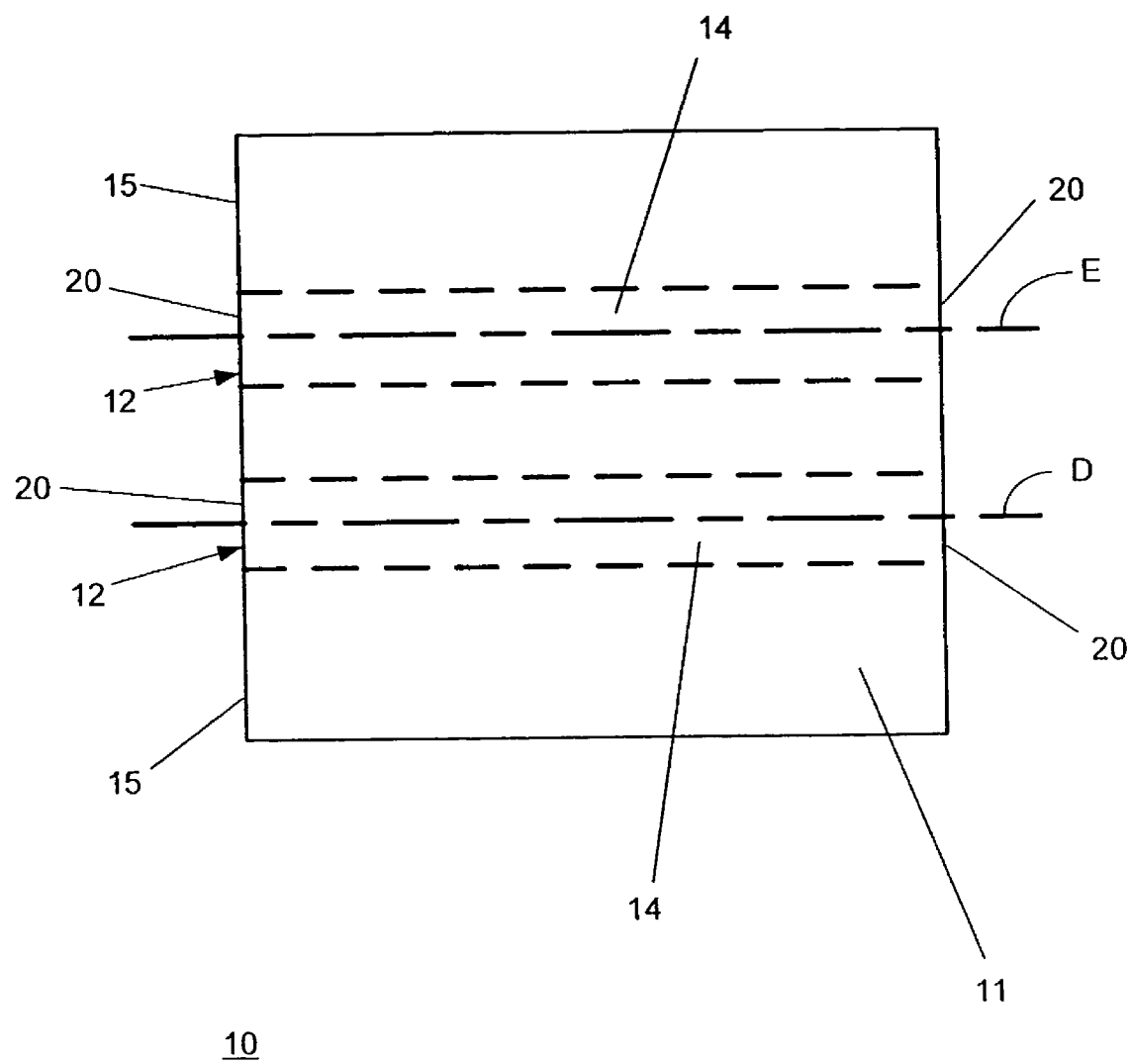
FIG. 4 is a sectional view of an anchor head in accordance with an alternate arrangement.

FIG. 4 is a sectional view of an anchor head 11 in accordance with an alternate arrangement of which the cross sectional shape of the head 11 is rectangular, without recesses being present. For the arrangement shown, void regions 14 of eyelets 12 extend along respective central axes D and E similar to the arrangement of FIG. 3 but lateral surfaces 15 are located at a greater relative distance along the central axes D, E.

Figure 5:
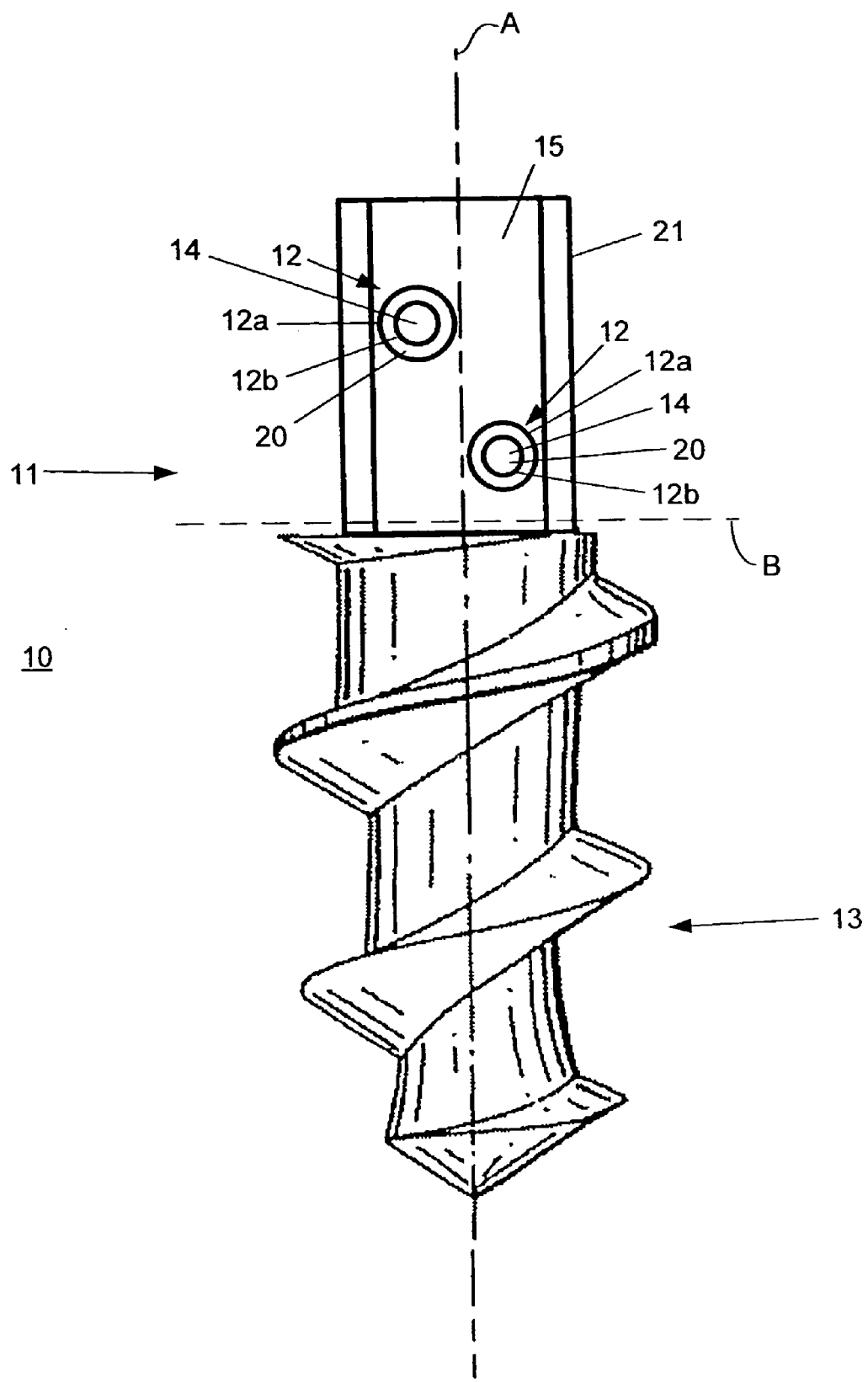
FIG. 5 is a frontal view of a suture anchor in accordance with a further arrangement.

FIG. 5 is a frontal view of a suture anchor 10 in accordance with a further arrangement in which eyelets 12 are counter-bored. The arrangement shown is similar to that of FIG. 1 in that each eyelet 12 is offset, or spaced apart, from the other a distance along the longitudinal axis A and also a distance in a direction transverse to the longitudinal axis A. The eyelets 12 may have a counter-bored configuration, indicated respectively by outer and inner diameters 12a and 12b. Such counter bores for eyelets 12 may facilitate reduced damage to a suture and/or reduce manufacturing costs of the suture anchor 10.

Figure 6:
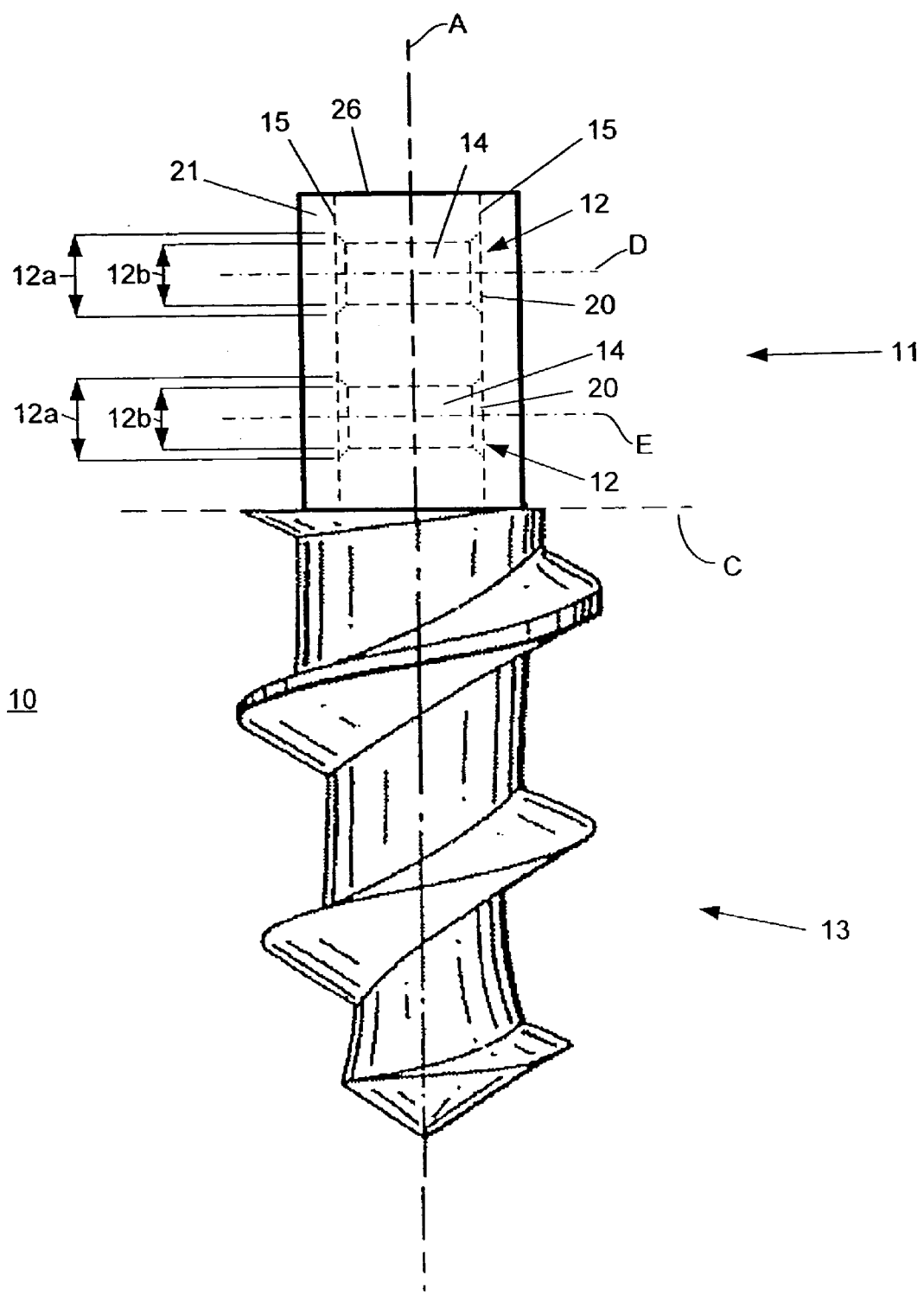
FIG. 6 is a side view of the suture anchor of FIG. 5.

FIG. 6 is a side view of the suture anchor 10 of FIG. 5. As shown, eyelets 12 have void regions 14 extending along respective central axes D and E between lateral surfaces 15 of the anchor head 11. Each eyelet 12 has a counter bored opening onto the lateral surfaces 15 of the anchor head 11, as indicated by outer diameter 12a and inner diameter 12b along respective central axes D and E.

Figure 7:
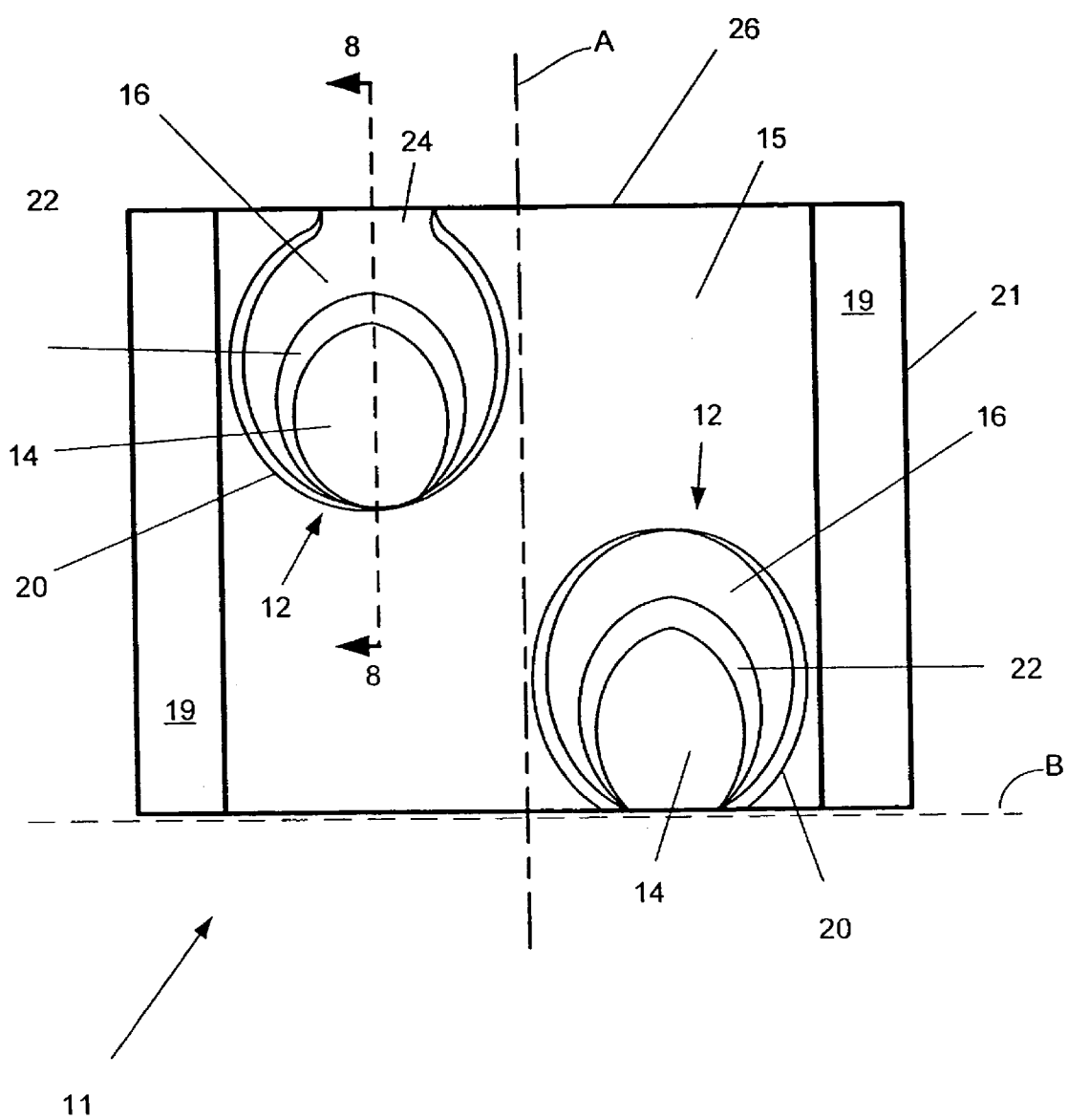
FIG. 7 is a frontal view of an anchor head with parabolic eyelets in accordance with another arrangement of the disclosure.

Referring to FIG. 7, a frontal view is shown of a suture anchor head 11 that includes eyelets having a parabolic shape in a cross section transverse to a suture anchor longitudinal axis A, in accordance with a further arrangement of the present disclosure. The anchor head 11 includes two eyelets 12 that are offset, or spaced apart, from one another a distance along the longitudinal axis A and also a distance in a direction transverse to the longitudinal axis A. Eyelets 12 include void regions 14 with openings 20 onto lateral surfaces 15 of the anchor head 11, similar to the other arrangements.

The void regions 14 of the eyelets 12 shown may include a variable cross section. For example, each void region 14 may include an outer region, indicated by surface 16, and an intermediate void region, indicated by surface 22. The outer void regions 16 may each have a defining surface that has a contoured or rounded shape, e.g., a segment of a desired conic surface. Each eyelet 12 may also include intermediate void regions 22, as shown, extending between the outer void regions 16 and the central void region 14. Defining surfaces of the intermediate void regions 22 for each eyelet 12 may be any suitable shape in cross section, e.g., circular cylindrical, elliptical, etc.

With continued reference to FIG. 7, an eyelet 12 may include chamfered or radiused cut-outs 24 extending between the openings of the eyelet 12 and an end or top surface 26 of the anchor head 11. Such cut-outs 24 may help to increase the angle of approach for a suture threaded through the openings 20 of the eyelet 12 and reduce stresses on the suture. Preferably all edges of the anchor head 11 that may come into contact with a suture are rounded to further protect a sutures threaded through the eyelets 12. Example of such locations on an anchor head 11 include between the cut-outs 24 and the end surface 26, between the lateral surfaces 15 and the outer void regions 16, between the outer void regions 16 and the intermediate void regions 22, and between the intermediate void regions 22 and the central void region 14.

Figure 8:
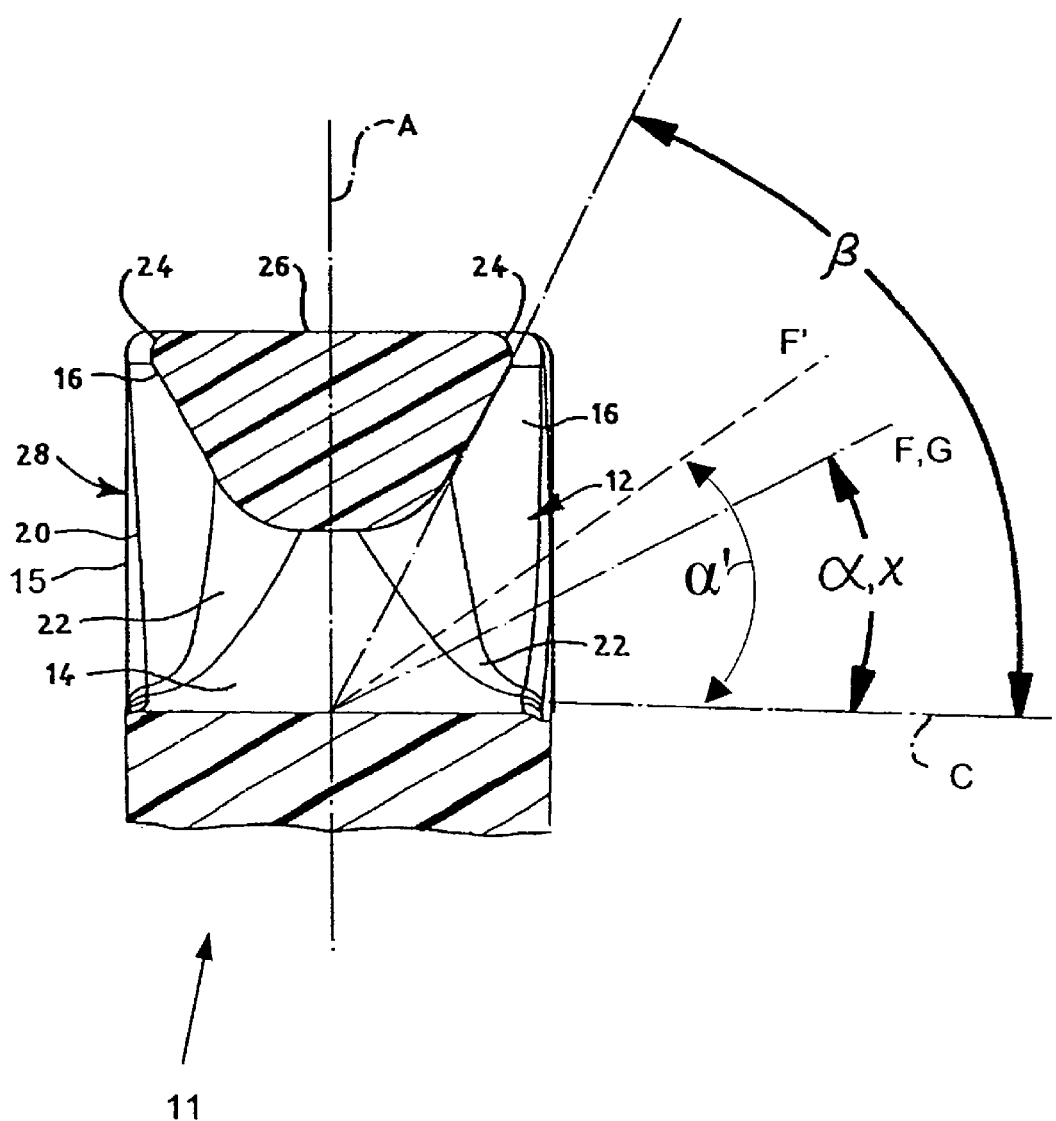
FIG. 8 is a sectional view of the anchor head of FIG. 8 in the direction of cutting plane 8-8.

FIG. 8 is a sectional view of the anchor head 11 of FIG. 7 in the direction of cutting plane 8-8. Outer void regions 16 are shown extending between the lateral surfaces 15 of the anchor head 11 and intermediate void regions 22, which are located on opposing sides of the central void region 14. The outer void regions 16 may each have a defining surface that has a contoured or rounded shape, e.g., a segment of a desired conic surface. The intermediate and outer void regions may have respective central axes F and G. The outer void region surface 16 may have an included angle β, which may in some arrangements be positioned in a plane that includes suture-direction axis C (which is orthogonal to both the longitudinal A axis and lateral axis B of FIG. 7). The central axis F may extend an angle χ with respect to axis C and central axis G may extend at an angle α with the respect to axis C. The outer and intermediate void regions 16, 22 may be shaped as desired to achieve particular locations of the respective central axes F and G. Alternate angle α' and central axis F' show one example.

In preferred arrangements, the central axes F and G may extend within a plane formed by the longitudinal axis A and the suture-direction axis C. In preferred arrangements, α and χ are each equal to thirty degrees with respect to axis C, causing axes F and G to be collinear. In preferred arrangements, the surfaces of the outer void regions 16 each are shaped as a segment of a conic surface having an included angle β equal to about sixty degrees. In certain arrangements, the outer void regions 16 are shaped such that a cross-section of the eyelet 12 along a plane extending normal to the longitudinal axis A is substantially parabolic, for optimal contact with a suture. Consequently, the openings 20 of the eyelets 12 may have elliptical cross section parallel to lateral surfaces 15 of the anchor 10.

Figure 9:
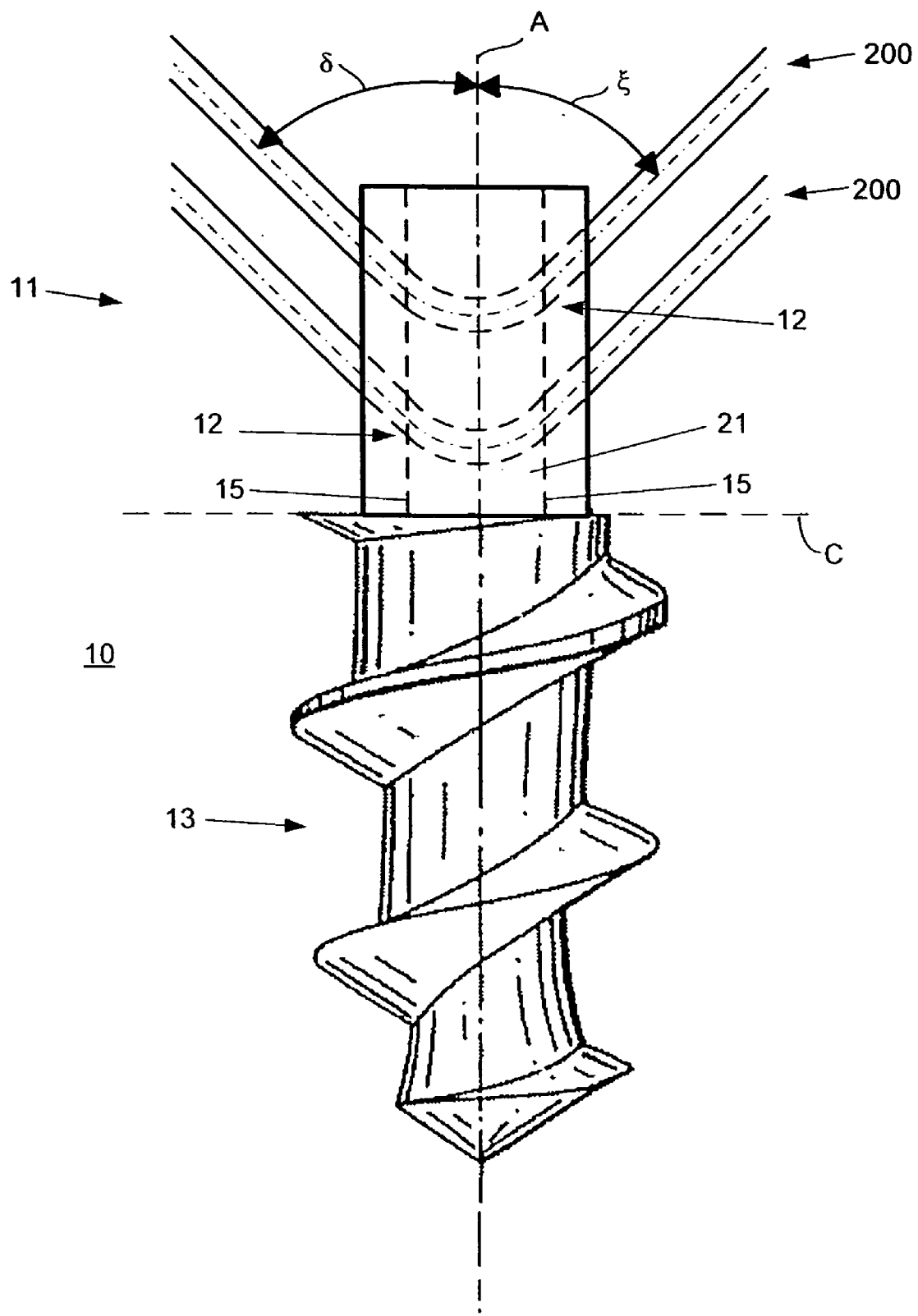
FIG. 9 is a side view of a suture anchor having parabolic eyelets similar to those shown in FIG. 7.

FIG. 9 is a side view of a suture anchor 10 having parabolic eyelets 12 similar to those shown in FIG. 7. The figure shows the curved paths, or arcs, that sutures 200 may follow when passing through the eyelets 12. The path of each suture 200 is aligned substantially along a suture-direction axis C, where suture-direction axis C is orthogonal or normal to longitudinal axis A of the anchor 10. Passing through the eyelets 12, each suture 200 may have an entry angle δ and an exit angle ζ between their respective central axes and the longitudinal axis A. By appropriate shaping of the eyelets 12, the entry and exit angles, δ and ζ, may be selected as desired. The configuration of the void regions 14 as shown allows for a gentle lead in and minimal damage to sutures 200 threaded through the eyelets 12, especially when the entry angles δ and exit angles ζ for receiving the sutures are each about forty-five degrees with respect to a longitudinal axis A of the anchor 10.

While shown as substantially similar, the entry and exit angles, δ and ζ, may differ from one another for a particular eyelet 12 and between different eyelets 12. Further, the various cross sections of the eyelets 12 and radius of curvature provided to the sutures 200 may differ from eyelet 12 to eyelet 12 with the suture anchor 10.

Figure 10:
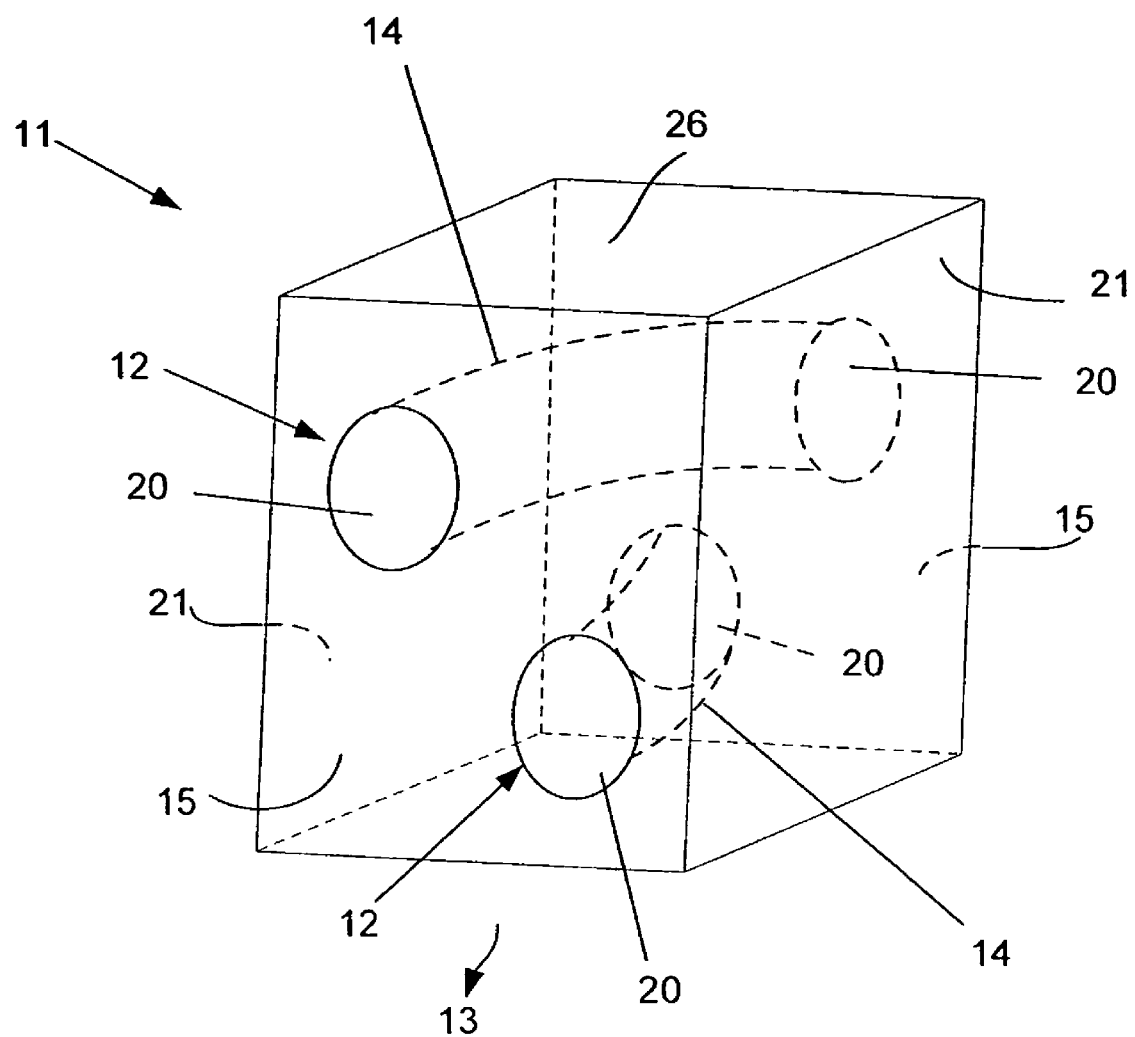
FIG. 10 is a perspective view of another arrangement of a suture anchor head in accordance with the present disclosure.

FIG. 10 is a perspective view of a further arrangement of a suture anchor head 11 that includes offset eyelets 12, each including a void region 14 extending about a central axis that is not a straight line. For example, each eyelet 12 may be configured about a central axis extending on a curved path, as shown, that spans the length of sides 21 between the lateral surfaces 15. The axis may have any desired configuration, such as for example, a circular arc, a serpentine shape, an irregular shape, a corkscrew shape (in which case the eyelets would twist about one another), etc. While not shown, a threaded body, e.g., similar to body 13 of FIG. 1, would be connected to the anchor head 11, opposite the top surface 26, for insertion into a bone segment.

Figure 11A:
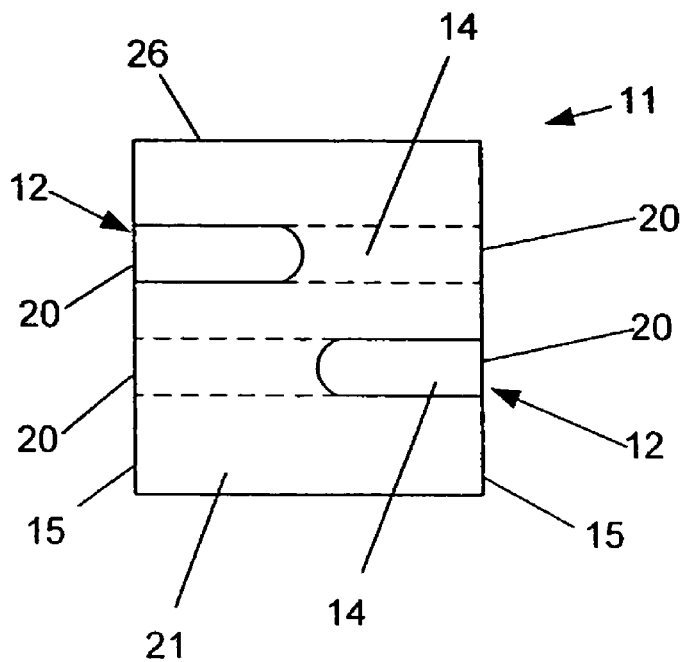
FIGS. 11A-B are side and top section views, respectively, of a suture anchor head similar to the one of FIG. 10.
Figure 11B:
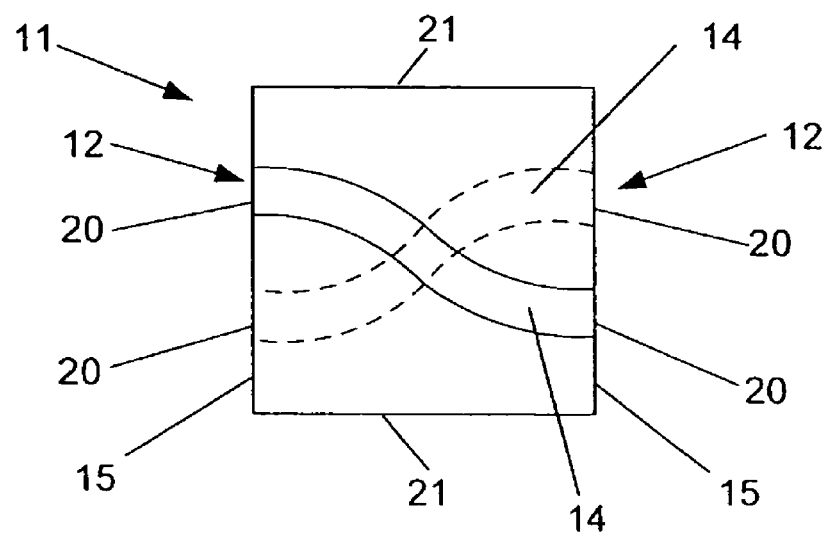

FIGS. 11A-B are side and top section views, respectively, of a suture anchor head 11 similar to the one in FIG. 10. The side section view of FIG. 11A, taken from near the mid point of the width of the suture anchor head 11, shows the two eyelets 12 transitioning from open to closed (or hidden) portions due to the curved nature of the void regions 14. FIG. 11B shows a top section view from a cutting plane bisecting the top eyelet 12. The eyelets 12 each extend along a sinusoidal or "S"-like central axis from one lateral surface 15 to the other 15. From the perspective shown in FIG. 11B, i.e., in a direction parallel to the longitudinal axis, the eyelets 12 cross over one another near the midpoints of their respective void regions 14.

FIG. 12 is a frontal view of an alternate configuration of a suture anchor head 11 similar to the configuration shown in FIG. 1. The eyelets 12 shown, however, each have a different diameter, with the top eyelet 12 being substantially larger than the lower eyelet 12. As shown, the eyelets 12 may partially overlap one another in a direction along the longitudinal axis A, i.e., when projected onto a plane transverse to the longitudinal axis A.

Suture anchors 10 according to the present disclosure may be made from a suitably rigid and strong material. Such a material preferably has sufficient compatibility with the biological material in which it is to be implanted. For example, a suture anchor 10 can be constructed of a non-absorbable material such as titanium or stainless steel, or bio-absorbable material such as polymers, polyglycolic acid (PGA), poly-L-lactic acid (PLLA), polydioxanone (PDS), and poly-D,L-lactic acid (PDLLA), and their copolymers, tyrosine-derived polycarbonates and tricalcium phosphates. The bio-absorbable anchors are useful when the eyelet is deployed below the surface of a bone so that bone regrowth eventually takes over to hold the suture to the bone as the anchor is absorbed. The eyelets 12 of the suture anchors 10 may be formed by suitable techniques, including, but not limited to, machining and molding. Other suitable techniques for forming the eyelets are also contemplated within the scope of the present disclosure.

Figure 13:
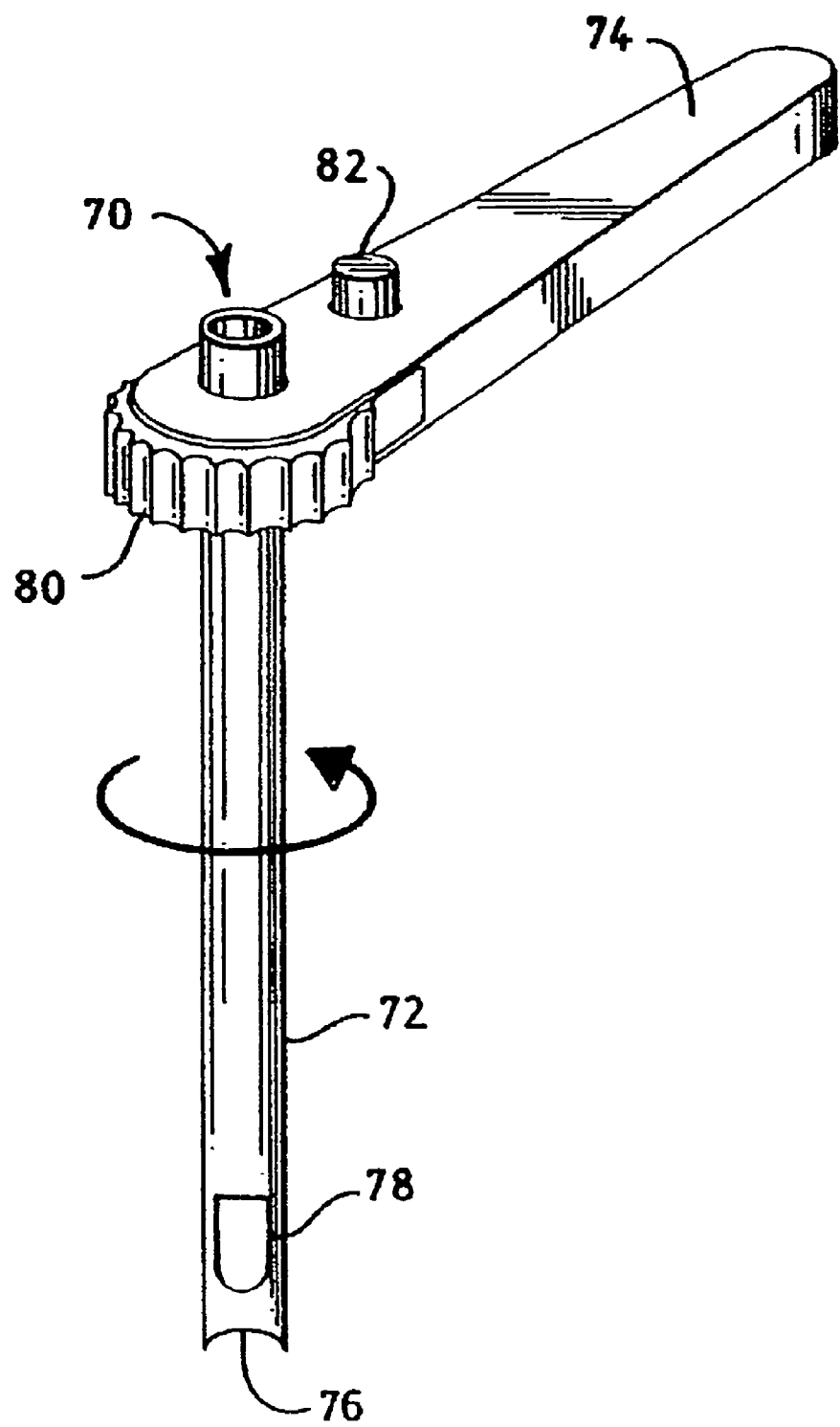
FIG. 13 is a perspective view of a drill guide constructed in accordance with the present disclosure.

FIG. 13 is a perspective view of a drill guide 70 constructed in accordance with the present disclosure. The drill guide 70 is for assisting in positioning a drill bit while drilling a hole in bone for receiving a suture anchor during an arthroscopic surgical procedure, such as shoulder arthroscopy. The drill guide 70 includes a tubular guide shaft 72 extending through a handle 74. The shaft 72 is for extending into the shoulder joint, for example, such that a tip 76 of the shaft can be positioned on the glenoid rim of the scapula bone of the shoulder joint, and includes a window 78 near the tip for properly aligning the shaft with the rim. The shaft 72 receives a drill bit there through for drilling a hole within the scapula. The shaft 72 can also be used to help position an anchor in the drilled hole and secure a suture to a suture anchor, e.g., suture anchor 10.

As shown, the drill guide 70 includes an adjustment wheel 80 secured to the shaft 72 within the handle 74 such that turning the wheel rotates the shaft to a desired position. The guide 70 also includes a button 82 in the handle 74. The button 82 may be used for preventing rotation of the wheel 80 and the shaft 72 when the button 82 is moved within the handle 74, allowing the shaft 72 to be maintained in a desired position during implantation of a suture anchor 10.

FIGS. 14 and 15 show a tubular drive tool 90 that is suitable for implantation of a suture anchor and that is constructed in accordance with the present invention. The tool 90 is for use in driving a suture anchor 10 into bone, while a suture 200 threaded through an eyelet 12 of the anchor extends through the hollow tool 90. The tool 90 includes a handle 92, a tube 94 extending from the handle to a distal end, and a drive socket 96 attached to the distal end of the tube.

As shown in FIGS. 14 and 15, the handle 92 of the drive tool 90 may include reference markings 102, 104 aligned with the recesses 100 of the drive socket 96. In the arrangement shown, the reference marks include lettering 104 and flat portions 102 formed on the handle 92. The reference marks 102, 104 of the drive tool 90 may help to identify the orientation of a suture 200 extending through the anchor 10 to improve suture and soft tissue alignment while placing the anchor.

FIGS. 16 and 17 show more detailed views of the drive socket shown in FIGS. 14 and 15. As shown, the drive socket 96 of the drive tool 90 may include inwardly facing surfaces 98 for gripping outwardly facing surfaces of the anchor head 28 of the suture anchor 10 for transferring torque from the drive tool 90 to the suture anchor 10. In addition, the inwardly facing surfaces 98 include recesses 100 positioned for alignment with the outer void regions 20 of the eyelets 12 of the anchor 10 and sized to receive a suture 200 passing through the eyelet. In the arrangement shown, the drive socket 96 is permanently attached to the tube 94, but can be provided as removably attachable to the tube.

Figure 18:
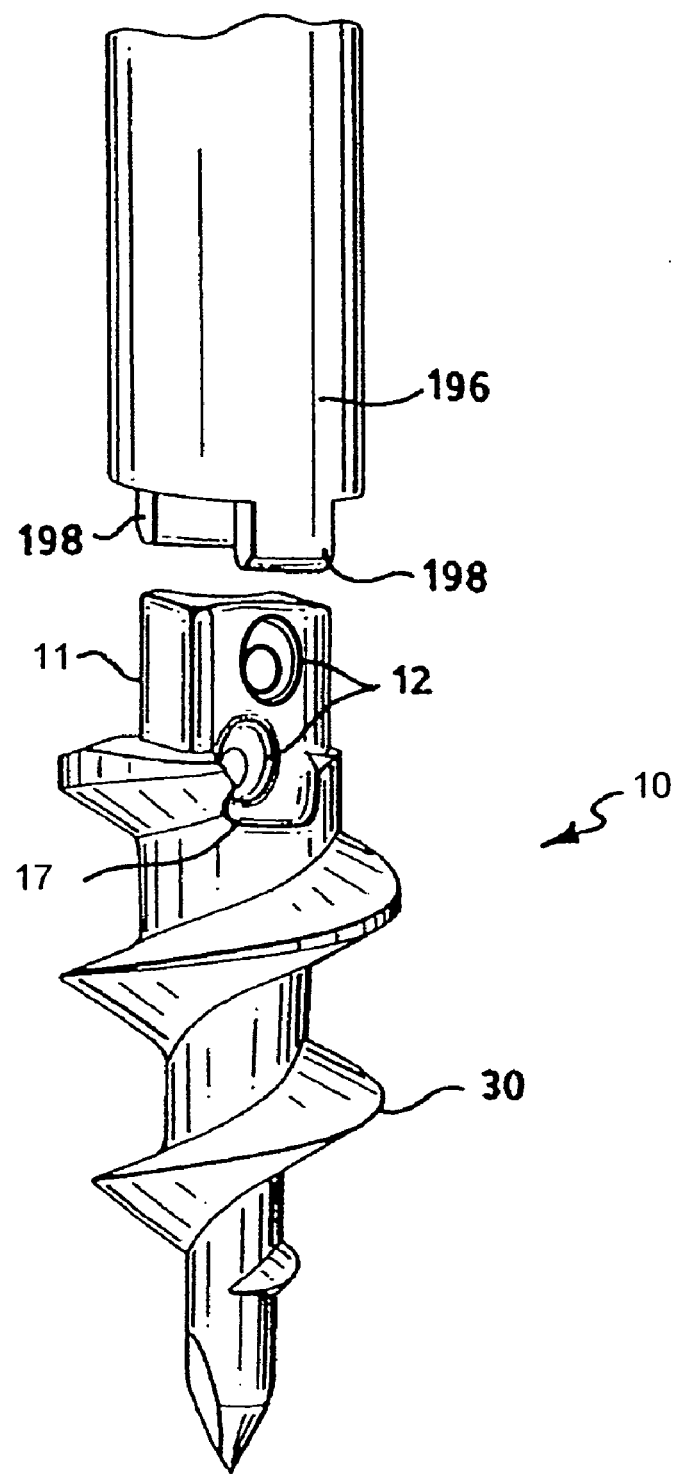
FIG. 18 is a perspective view of another tip of a drive tool constructed in accordance with the present disclosure shown being used with, for example, the suture anchor of FIG. 6.

FIG. 18 shows another drive socket 196 constructed in accordance with a further arrangement of the present disclosure. The drive socket 196 is similar to the drive socket 96 of FIGS. 11 and 12, but further includes at least two tabs 198 extending axially from a distal edge of the socket. The tabs 198 may be used for covering and protecting a suture (not shown) received in the anchor 10, while the anchor 10 is being screwed into a bone using the socket 196. As shown, the suture anchor 10 includes an axially extending recess 17 extending over each opening of the outer void regions of the eyelets 12 and the tabs 198 are aligned for receipt within the recesses 17 and adapted to receive a suture, e.g., suture 200, between the tabs 198 and the anchor 10, to mitigate damaging, e.g., crushing, of the suture between the socket 196 and the suture anchor 10.

The suture anchors, drill guide and drive tool described above can be included, individually or in any combination, as part of a surgical kit also including at least one length of suture (not shown) for a given suture anchor. The suture can be a monofilament or multifilament, braided suture. The suture may be bio-compatible and may be bio-absorbable if desired. In addition, one end of the length of suture may be deformed and shaped differently than the other end, such that a surgeon can distinguish the two ends of the suture length visually and by touch during a surgical procedure. For example, one end of the length of suture within the surgical kit can be deformed and shaped so that it is flat, while the other end is not deformed such that it remains cylindrical.

Accordingly arrangements of the present disclosure address needs seen for the prior art by providing improved suture anchors and surgical kits including the same. By employing multiple eyelets that are offset from one another along an axis transverse to a longitudinal axis, anchor heads may have increased strength and resistance to shear failure, leading to overall improvements in strength for a suture anchor.

It should be understood that the presently disclosed suture anchors, drill guide, driver tool, and surgical kits, can be embodied in other specific forms without departing from the spirit or essential characteristics thereof. For example, suture anchors according to the present disclosure may be made of a suitable metal or plastic. Furthermore, plastics may be used that dissolve in a body in a harmless manner a suitable period after being secured therein, such that the suture anchors and sutures do not have to be removed by medical personnel. In addition, offset eyelets formed in accordance with the present disclosure can be formed in an insert for insertion into an anchor after the anchor has been fixed within a bone, as opposed to being formed directly in the anchor. Moreover, while the previous description has referred to suture anchors having two offset eyelets, a plurality of offset suture anchors of any numbers, e.g., three, four, etc., may be utilized for a suture anchor according to the present disclosure.

The present disclosure describing suture anchors and surgical kits, therefore, is to be considered in all respects as illustrative and not restrictive, the scope of the invention being indicated by the appended claims rather than by the foregoing description. All changes that come within the meaning and range of he equivalency of the claims are therefore intended to be embraced therein.

What is claimed is:

1. A suture anchor for securing soft tissue to bone, comprising:
   a first suture;
   a second suture;
   a threaded body connected to an anchor head, the threaded body and anchor head extending along a longitudinal axis; and
   a plurality of eyelets extending between opposing first and second lateral surfaces of the anchor head for receiving multiple sutures, wherein a first eyelet of the plurality of eyelets is configured to receive the first suture, wherein a second eyelet of the plurality of eyelets is configured to receive the second suture, such that each of the first and second sutures is adjustable independently of other adjacent sutures;
   wherein the first lateral surface is parallel to the second lateral surface;
   wherein each eyelet comprises a first opening on the first lateral surface and a second opening on the second lateral surface, said first and second openings of each eyelet being offset transversely with respect to the longitudinal axis;
   wherein each eyelet defines a void region that has a central axis,
   wherein on a pair-wise basis the first openings of the eyelets are offset along the longitudinal axis and transversely with respect to the longitudinal axis, and
   wherein on a pair-wise basis the second openings of the eyelets are offset along the longitudinal axis and transversely with respect to the longitudinal axis.

2. A suture anchor according to claim 1, wherein each eyelet comprises two outer void regions, each outer void region extending from one of the lateral surfaces of the head, having a central axis forming an acute angle with the longitudinal axis, and having a surface shaped as a segment of a conic surface extending about the central axis of the outer void region and tapering inward towards the longitudinal axis, and a central void region extending between the outer void regions.

3. A suture anchor according to claim 2, wherein the central axis of each outer void region of the eyelet extends within a plane formed by the longitudinal axis and a suture-direction axis of the eyelet.

4. A suture anchor according to claim 2, wherein the central axes of the outer void regions extend at an angle of about sixty degrees with respect to the longitudinal axis.

5. A suture anchor according to claim 1, wherein the openings of each eyelet are elliptical in cross section parallel to the lateral surfaces.

6. A suture anchor according to claim 1, wherein the body includes cut-outs extending between openings of the eyelet and an end surface of the anchor head.

7. A suture anchor according to claim 6, wherein each of the cut-outs extends between corners formed by the end surface and a lateral surface of the anchor head.

8. A suture anchor according to claim 1, wherein the surfaces of the outer void regions each form a segment of a conic surface having an included angle of about sixty degrees.

9. A suture anchor according to claim 1, wherein the eyelet includes a counter bore.

10. A suture anchor according to claim 1, wherein the threaded body is self-tapping.

11. A suture anchor according to claim 10, wherein the threaded body includes a selfdrilling tip at the end of the body.

12. A suture anchor according to claim 1, made from bio-compatible material.

13. A suture anchor according to claim 1, made from bio-absorbable material.

14. A suture anchor according to claim 1, wherein a central void region of the eyelet is cylindrical.

15. A suture anchor according to claim 1, wherein the eyelet further includes intermediate void regions extending between respective outer void regions and a central void region.

16. A suture anchor according to claim 15, wherein the intermediate void regions are cylindrical.

17. A suture anchor according to claim 16, wherein central axes of the intermediate void regions extend at an angle of about sixty degrees with respect to the longitudinal axis of the body.

18. A suture anchor according to claim 1, wherein one eyelet has a central axis that is not a straight line.

19. A suture anchor according to claim 18, wherein the central axis is curved.

20. A kit including a suture anchor according to claim 1, and further comprising a drill guide having: a handle; a hollow guide shaft rotatably secured to the handle, the guide shaft having a tip and an alignment window adjacent the tip; an adjustment wheel radially extending from the shaft; and a button positioned within the handle and movable to a locked position preventing rotation of the adjustment wheel.

21. A kit according to claim 20, further including at least one length of suture.

22. A kit according to claim 21, wherein the suture is a monofilament.

23. A kit according to claim 22, wherein one end of the length of suture is deformed.

24. A kit according to claim 22, wherein the suture is bio-compatible.

25. A kit according to claim 24, wherein the suture is bio-absorbable.

26. A kit including a suture anchor according to claim 1, the kit further comprises a tubular drive tool having: a handle; a tube extending from the handle to a distal end; and a drive socket attached to the distal end of the tube and including inwardly facing surfaces for gripping outwardly facing surfaces of the drive head of the suture anchor for transferring torque from the drive tool to the suture anchor, and wherein the inwardly facing surfaces include recesses positioned for alignment with the outer void regions of the eyelet of the anchor and sized to receive a suture passing through the eyelet.

27. A kit according to claim 26, wherein the drive socket is removably attached to the tube.

28. A kit according to claim 26, further including at least one length of suture.

29. A kit according to claim 28, wherein the suture is a monofilament.

30. A kit according to claim 28, wherein one end of the length of suture is deformed.

31. A kit according to claim 28, wherein the suture is bio-compatible.

32. A kit according to claim 28, wherein the suture is bio-absorbable.

33. A kit according to claim 26, wherein the drive socket further includes at least two tabs extending axially from a distal edge of the socket.

34. A kit according to claim 33, wherein the suture anchor includes an axially extending recess extending over each opening of the outer void regions of the eyelet for receiving the tabs of the drive socket.

35. A suture anchor according to claim 18, wherein the central axis is substantially sinusoidal.

36. A suture anchor according to claim 1, wherein the central axis has a shape chosen from the group consisting of: a circular arc, a serpentine shape, an irregular shape, and a corkscrew shape.

37. A suture anchor according to claim 1, wherein projections onto a plane transverse the longitudinal axis of the central axes of at least two eyelets intersect at least at one point.

38. A suture anchor according to claim 1, wherein at least two of the eyelet openings located on the same lateral surface differ in size.

39. A suture anchor according to claim 37, wherein a projection of the at least two eyelet openings onto the plane transverse the longitudinal axis at least partially overlap each other.

40. The suture anchor of claim 1, wherein the plurality of eyelets is configured to permit each of the multiple sutures to be adjusted independently without contacting the other adjacent sutures.

41. A suture anchor system comprising:
a first suture;
a second suture;
a threaded body connected to an anchor head, the threaded body and anchor head extending along a longitudinal axis;
a first eyelet extending between opposing first and second lateral surfaces of the anchor head, wherein the first suture extends through the first eyelet;
a second eyelet extending between the first and second lateral surfaces, wherein the second suture extends through the second eyelet;
wherein the first eyelet is parallel to the second eyelet;
wherein the first eyelet and the second eyelet permit each of the first and second sutures to be adjusted independently;
wherein the first eyelet includes a first opening on the first lateral surface and a second opening on the second lateral surface, wherein the first and second openings are offset transversely with respect to the longitudinal axis, wherein the second eyelet includes a third opening on the first lateral surface and a fourth opening on the second lateral surface, wherein the third and fourth openings are offset transversely with respect to the longitudinal axis;

wherein on a pair-wise basis the first opening and the third opening are offset along the longitudinal axis and transversely with respect to the longitudinal axis; and wherein on a pair-wise basis the second opening and the fourth opening are offset along the longitudinal axis and transversely with respect to the longitudinal axis.

42. The suture anchor system of claim 41, wherein after implementation of the suture anchor system, the first and second sutures can be adjusted without contacting each other.

43. The suture anchor system of claim 41, further comprising:

a third suture; and a third eyelet extending between the first and second lateral surfaces of the anchor head, wherein the third suture extends through the third eyelet, wherein after implementation of the suture anchor system, the first, second, and third sutures can be adjusted without contacting each other.

* * * * *